United States Patent [19]

Poler

[11] Patent Number: 4,571,039

[45] Date of Patent: * Feb. 18, 1986

[54] EYE-MEDICATING CONTACT-LENS CONSTRUCTION

[76] Inventor: Stanley Poler, 78 E. Second St., New York, N.Y. 10003

[*] Notice: The portion of the term of this patent subsequent to Sep. 6, 2000 has been disclaimed.

[21] Appl. No.: 485,395

[22] Filed: Apr. 15, 1983

[51] Int. Cl.<sup>4</sup> ......................... A61M 31/00; G02C 7/04
[52] U.S. Cl. ............... 351/160 H; 351/160 R; 604/893; 604/895
[58] Field of Search ............... 604/893, 895; 351/160 R, 160 H, 161

[56] References Cited

U.S. PATENT DOCUMENTS

| | | | |
|---|---|---|---|
| 3,926,188 | 12/1975 | Baker et al. | 604/893 |
| 3,957,049 | 5/1976 | Neefe | 604/895 |
| 3,973,837 | 8/1976 | Page | 351/160 R |
| 4,402,579 | 9/1983 | Poler | 351/160 R |

*Primary Examiner*—John K. Corbin
*Assistant Examiner*—Scott J. Sugarman
*Attorney, Agent, or Firm*—Hopgood, Calimafde, Kalil, Blaustein & Judlowe

[57] ABSTRACT

The invention contemplates eye-medicating contact-lens constructions wherein a small central optical component is retained by surrounding fenestrated haptic structure which is the vehicle for eye medication. The haptic structure is initially flat but axially flexible as to be self-adapting to the surface of the cornea and to be self-retaining of its position, via moisture at the surface of the cornea. Medication carried by the haptic is made available to the surface of the cornea by mild pumping action of haptic structure on corneal fluid, the medication being drawn from storage in the haptic, by the wash of liquid involved in the pump action.

20 Claims, 8 Drawing Figures

EYE-MEDICATING CONTACT-LENS CONSTRUCTION

BACKGROUND OF THE INVENTION

The invention relates to structures which are self-adherent to the surface of the cornea and which are the vehicle of one or more medicaments for the eye.

In my U.S. Pat. No. 4,377,329, contact-lens configurations are described wherein the lens is a relatively small central component, and a surrounding haptic is a second component. The haptic is substantially fenestrated and is so thin and flexible that, although normally flat, being formed from flat sheet material, it is self-adapting to the curvature of the cornea, and it remains removably adhered to the cornea via normal moisture on the surface of the cornea. The entire structure is so thin as to cause no discomfort, in spite of normal eyelid action, and the eyelid action operates upon the fluid suspension of the haptic in such manner as to assure circulation of fluid in the moist region between all parts of the haptic and the cornea.

In a recent article by Robert Hildebrand, "Polymers Release Drugs Continuously", *High Technology*, January 1983, pages 28 to 31, new drug systems are described for delivery of medical dosages at desired rates for extended periods of time. In particular, bio-compatible polymers are described wherein particular drugs are built into the polymer for diffusion, as from a capsule, in the course of time. Among the products described is a relatively expensive one for use in the eye, wherein a plastic disk sits continuously on the eyeball behind the lower eyelid, releasing pilocarpine for glaucoma therapy.

BRIEF STATEMENT OF THE INVENTION

It is an object of the invention to produce a contact-lens construction with an eye-medicating feature of the character indicated.

It is a specific object to meet the above object with structure which is self-adapting and removably self-adherent to the surface of the cornea and which does not optically interfere with normal operation of the eye.

A general object is to achieve these objects with structure which is inherently simple, safe and inexpensive.

The invention achieves the above objects with contact-lens configurations in which a relatively small central lens element is surrounded by fenestrated haptic structure which is initially flat and thin and so compliant as to be removably self-adapting to the curvature of the cornea, adhering solely via moisture on the cornea. The haptic structure and the lens element may be separate parts, in which case the haptic may be of hydrophilic, foraminated, pocked or other material having an ability to store medication, for slow release in the presence of natural moisture of the eye, and aided by normal blinking eyelid action. If the lens element and the haptic are integrally formed from the same sheet of material, then the fenestrations and/or body of the haptic may be foraminated or pocked for such storage and slow release of the medication.

DETAILED DESCRIPTION

The invention will be described in detail for several embodiments, in conjunction with the accompanying drawings, in which.

Figure 1:
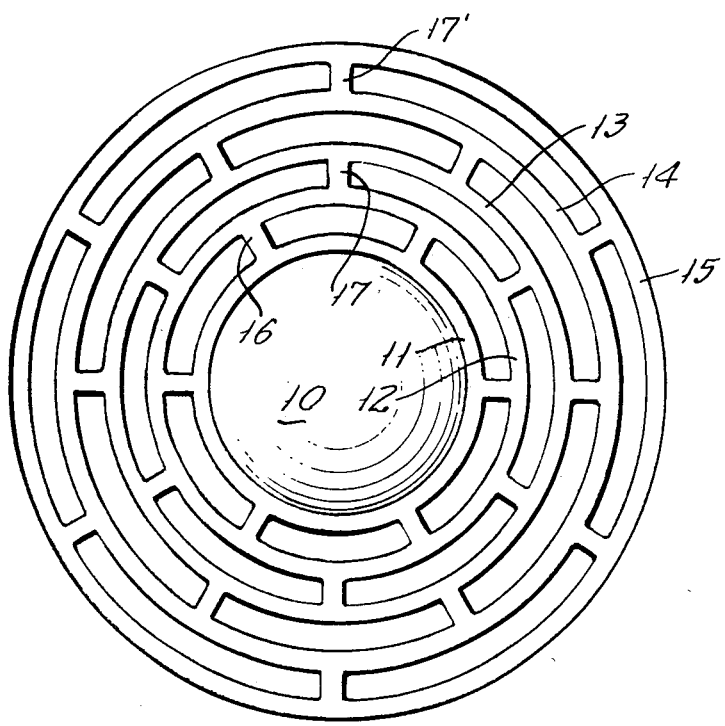
FIG. 1 is a plan view of an eye-medicating contact lens of the invention.
Figure 2:
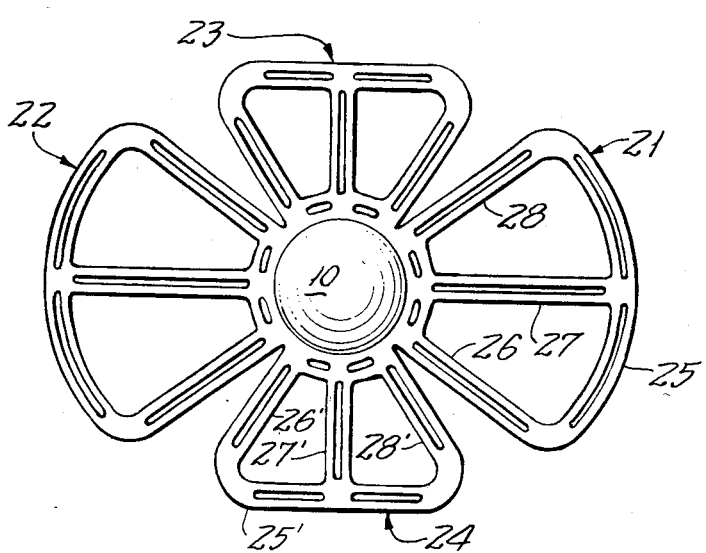
FIG. 2 is a view similar to FIG. 1, for a different embodiment.

FIGS. 1 and 2 illustrate two general kinds of contact-lens constructions wherein a small circular lens element 10 is surrounded by annular haptic structure which features substantial fenestration of initially flat thin plastic sheet material, having the ability to not only self-adapt and removably adhere to the surface of the cornea but also to retain and slowly release medication when thus adhered.

The embodiment of FIG. 1 features circumferential continuity of the haptic, providing a succession of radially spaced concentric rings 11-12-13-14-15, about the central lens 10. The lens 10 and its supporting haptic may be separate parts, assembled to each other, in which case reference is made to my copending application Ser. No. 225,349, filed Jan. 15, 1981, now U.S. Pat. No. 4,435,050, for illustrative detail; or the lens 10 and its supporting haptic may be integrally formed from the same single sheet of starting material, in which case reference is made to my copending application Ser. No. 288,217, filed July 29, 1981, now U.S. Pat. No. 4,402,579, for illustrative detail.

The concentric rings 11-12-13-14-15 are integrally connected by first sets of angularly spaced radial connectors 16-16' between rings 11-12 and 13-14, and by further sets of such connectors 17-17' between rings 12-13 and 14-15; the sets 16-16' and 17-17' are in angularly staggered interlace. The lens diameter is desirably 6 to 8 mm, for ample lens-aided normal vision, and the outer diameter of outer ring 15 may be 12 to 14 mm. The planiform of the haptic of FIG. 1 will be recognized from my copending application, Ser. No. 467,436, filed Feb. 17, 1983, to which reference is made as to self-adaptation and other features in application to the surface curvature and moisture of the cornea.

The haptic configuration of FIG. 2 will be recognized from my said U.S. Pat. No. 4,377,329. In this configuration, an inner-ring portion 20 is circumferentially continuous at the region of lens (10) support, and opposed pairs of fenestrated feet 21-22 and 23-24 extend radially. Each foot comprises an outer arcuate or transverse tie, as at 25 (25'), integrally connecting three radial legs 26-27-28 (26'-27'-28'), and elongate slots in all component members 20 to 28 of the haptic provide passages for fluid access (e.g., fluid pumping) or medication storage, in addition to enhancing the inherently flexible and contour-adapting nature of the construction.

The described haptic structures will be understood to be normally flat, each being formed from a single sheet of thin plastic material inert to body fluids. The formative process may be a selected one of photo-etch, ion-erosion, and the like procedures which I have described in U.S. Pat. No. 4,080,709, being adapted to production in multiple upon and from a single sheet of suitable plastic. Materials presently considered suitable in such sheets illustratively include cellulose acetate butyrate, cellulose acetate propionate, silicones and silicone acrylates, polymethypentene, polytrichloroethylene, polyvinylidenefluoride and H.E.M.A., the latter four being hydrophilic and therefore suitable for soaked up storage of medication, such as boric-acid solution commonly used for relief of eye strain or a "burning" sensation.

Figure 3:
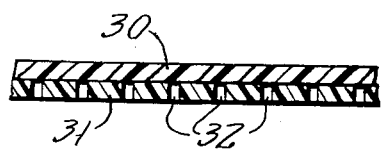
FIG. 3 is an enlarged fragmentary sectional view to illustrate a laminated construction for haptic regions in either of the forms of FIGS. 1 and 2.

FIG. 3 illustrates that either of the above-described types of haptic may in fact be the product of bonding plural (e.g., two) very thin plies 30-31 to each other. In the form shown, one (31) of these plies is pocked with foraminations, defining spaced pockets 32 which are receptors for the storage and slow releasability of medication, primarily directed via surface moisture on the cornea, or on the inner surface of the upper eyelid, depending upon whether the pockets 32 face inwardly or outwardly when applied to the corneal surface.

FIG. 3 can also be taken to illustrate a configuration wherein the ply 30 is the single ply from which both the optic and the haptic are formed, as in the manner set forth in my copending application, Ser. No. 288,217, filed July 29, 1981, the pocketed ply 31 being fenestrated to accord and register with fenestration of the haptic portion of ply 30. In this event, the pockets 32 again serve as receptors for the storage and slow releasability of medication.

Figure 4:
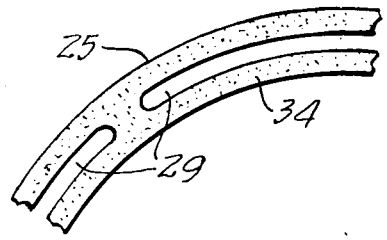
FIG. 4 is an enlarged fragmentary plan view of a haptic region to illustrate another construction for either of the forms of FIGS. 1 and 2.

FIG. 4 illustrates a fragment of slotted haptic structure, e.g., arcuate connection 25 of FIG. 2, wherein the full thickness of a single ply is foraminated for the indicated purposes. As seen in FIG. 4, the foraminations are in great number and much smaller than the size of slots 29 of ring 25, the foraminations being shown in FIG. 4 by stippling 34.

Figure 5:
FIGS. 5 to 8 are further views similar to FIG. 3 to illustrate more embodiments.

FIG. 5 is another example of applying the invention to a configuration wherein a single ply 50 may serve either as the material for the haptic alone or as the material for both the optic and the haptic, as in said copending application Ser. No. 288,217. In the case of FIG. 5, however, the haptic portion of the single ply is only partially etched or otherwise eroded from one side, to define receptor pockets 51 for storage and slow releasability of medication.

Figure 6:
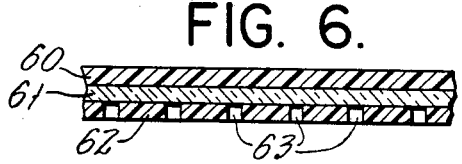

In the configuration of FIG. 6, a single ply 60 may serve either as the material for the haptic alone or as the material for both the optic and the haptic. This ply is coated with a medication layer 61, which in turn is covered with a thin layer 62 having foraminations 63 through which moisture of the eye can weep for controlled pick-up and external release of medication. If the layer 62 is of plastic material, then the foraminations 63 will remain with constant open area; on the other hand, if the layer 62 is a dissolvable membrane, as of gelatin, then the foraminations 63 will enlarge in area in the course of the fluid flow which releases medication, thus progressing the access to stored medication as the medication is consumed.

Figure 7:
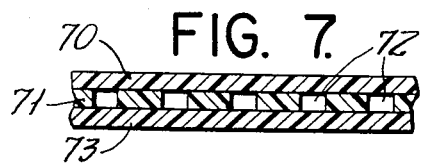

In the arrangement of FIG. 7, a single ply 70 may serve either as the material for the haptic alone or as the material for both the optic and the haptic. A foraminated ply 71 is adhered to the haptic of ply 70, with medication loaded in the pockets 72 of layer 71, all as described for the FIG. 3 situation. However, in FIG. 7, a slower rate of medication release is obtained by applying a thin layer 73 over the loaded ply 71. Layer 73 is characterized by a dense pattern of pinholes (denoted by upright lines in FIG. 7), the pinholes being each in the order of 0.001-inch diameter and of very much smaller sectional area, e.g., 10 percent of the area of each of the foraminations which define pockets 72 in ply 71.

Figure 8:
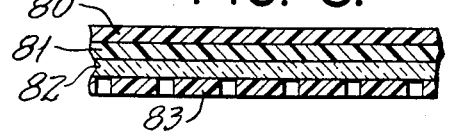

In the arrangement of FIG. 8, the lens and haptic are formed from an initially laminated starting material, comprising a relatively hard layer 80 which serves for ultimate formation of the lens component, and a relatively soft pliable plastic layer 81 which serves for ultimate formation of the associated haptic; such constructions are shown and described in my copending application, Ser. No. 319,622, filed Nov. 9, 1981, now U.S. Pat. No. 4,450,593, and therefore further description is not now needed. To this laminated starting material (layers 80-81), a medication layer 82, and a covering layer 83 are applied, in the manner and for the purposes described in connection with layers 61-62 of FIG. 6.

The haptic portions of described contact lenses will be seen as illustrative vehicles for medication to serve via the surface moisture of the cornea. All described haptics are not only self-adapting to curvature of the cornea but are also self-adherent via the surface moisture. Still further, the nature of all described structures is to flex by slight local twisting when the eyelid blinks, giving rise to mild pumping action on the surface liquid and thereby aiding in release and distribution of stored medication.

In the laminated-haptic situation, the haptic region of a ply (e.g., ply 31) not relied upon for lens 10 support may be a deliquescent carrier of the medication, or it may be merely "spongy" to a degree, whereby the user may remove his contact lens for a soaking in medication (e.g., boric-acid or other medicating solution) before reapplication to the eye.

It will be appreciated that among the indicated available sheet materials, there is some variation in strength, flexibility, and like properties, as a function of material thickness. Generally, however, it may be stated that thickness of the indicated haptics is in the order of 0.001 inch, and in the case of plied structure as in FIGS. 3 and 6 to 8, the thickness of individual plies 30-31 is in the order of 0.0005 inch.

It will also be appreciated that timed release of medication may be either primarily a function of sectional area of pockets or of foraminations, or it may be primarily a function of pocket depth, depending upon area/depth proportions upon the nature of the medication and of the eye-surface moisture condition of the patient for whom the medication is prescribed or intended.

While the invention has been described in detail for preferred forms, it will be understood that modifications may be made without departing from the scope of the invention.

What is claimed is:

1. A contact lens assembly adapted for self-adherent removable mounting to the cornea of an eye, comprising a circular lens element, and eye-medicating haptic means peripherally engaging and mounting said element, said haptic means being a fenestrated annulus of sheet material and being of such compliant action as to deform in continuous smooth conformance to the surface curvature of the cornea and to adhere thereto solely through contact with natural moisture of the surface of the cornea, and said annulus being adapted to carry medication releasable on contact with such moisture.

2. The lens assembly of claim 1, in which said sheet material is hydrophilic.

3. The lens assembly of claim 1, in which said sheet material contains medication impregnated therein.

4. The lens assembly of claim 1, in which medication is adhered to and within fenestrations of said annulus.

5. The lens assembly of claim 1, in which deliquescent medication is adhered to said annulus.

6. The lens assembly of claim 1, in which medication is adhered to both sides of said annulus.

7. The lens assembly of claim 1, in which medication is adhered to one side of said annulus, the other side having a surface texture which is visually different from the appearance of the medicated side.

8. The lens assembly of claim 1, in which said annulus comprises a peripherally continuous outer rim, with fenestrations of the annulus encompassed by said rim.

9. The lens assembly of claim 1, in which said annulus comprises a peripherally continuous inner ring which mounts said lens element, with fenestrations of the annulus radially outside said ring.

10. The lens assembly of claim 1, in which said annulus and said lens element are integrally formed from the same single sheet of material.

11. The lens assembly of claim 1, in which said annulus is characterized by fenestrated foot formations extending outward of said lens element at angularly spaced locations.

12. The lens assembly of claim 1, in which said sheet material is in the thickness range of 0.0005 to 0.002 inch.

13. The lens assembly of claim 1, in which said sheet material comprises at least two thin laminated sheets, one of which is foraminous, whereby the foraminated side is adapted to releasably retain medication.

14. The lens assembly of claim 13, in which the individual thickness of said laminated sheets is in the order of 0.0005 inch.

15. The lens assembly of claim 13, in which said laminated annulus is fenestrated, with fenestration openings larger than the foraminations.

16. The lens assembly of claim 13, in which one of said laminated sheets is soluble in moisture of the eye.

17. The lens assembly of claim 13, in which one of said laminated sheets is a protein substance.

18. The lens assembly of claim 13, in which one of said laminated sheets is gelatin.

19. The lens assembly of claim 13, in which said sheet material further includes a third thin laminated sheet which is porous and which otherwise covers the otherwise unlaminated side of said foraminated sheet.

20. The lens assembly of claim 1, in which at least one side of said haptic sheet is characterized by pockets open to said one side and terminating short of the other side of said haptic sheet.

* * * * *